(12) United States Patent
Ozaki et al.

(10) Patent No.: US 9,439,842 B2
(45) Date of Patent: Sep. 13, 2016

(54) USE OF ACID IN THE MANUFACTURE OF ORGANOPOLYSILOXANE

(71) Applicant: Dow Corning Toray Co., Ltd., Tokyo (JP)

(72) Inventors: Masaru Ozaki, Ichihara (JP); Seiji Hori, Ichihara (JP); Takatoshi Toyama, Ichihara (JP); Kazuhiko Kojima, Ichihara (JP); Tsunehito Sugiura, Ichihara (JP)

(73) Assignee: DOW CORNING TORAY CO. LTD., Tokyo (JP)

( * ) Notice: Subject to any disclaimer, the term of this patent is extended or adjusted under 35 U.S.C. 154(b) by 0 days.

(21) Appl. No.: 14/365,245

(22) PCT Filed: Dec. 4, 2012

(86) PCT No.: PCT/JP2012/081870
§ 371 (c)(1),
(2) Date: Jun. 13, 2014

(87) PCT Pub. No.: WO2013/089044
PCT Pub. Date: Jun. 20, 2013

(65) Prior Publication Data
US 2014/0356309 A1  Dec. 4, 2014

(30) Foreign Application Priority Data
Dec. 16, 2011 (JP) .................. 2011-275721

(51) Int. Cl.
| | |
|---|---|
| A61K 8/02 | (2006.01) |
| A61K 8/24 | (2006.01) |
| C08L 83/06 | (2006.01) |
| C08L 83/08 | (2006.01) |
| C08K 3/24 | (2006.01) |
| C08K 5/09 | (2006.01) |
| A61K 8/06 | (2006.01) |
| A61K 8/36 | (2006.01) |
| A61K 8/898 | (2006.01) |
| A61Q 5/00 | (2006.01) |
| C08G 77/08 | (2006.01) |
| C08G 77/16 | (2006.01) |
| C08G 77/26 | (2006.01) |

(52) U.S. Cl.
CPC . *A61K 8/24* (2013.01); *A61K 8/06* (2013.01); *A61K 8/36* (2013.01); *A61K 8/898* (2013.01); *A61Q 5/00* (2013.01); *C08K 3/24* (2013.01); *C08K 5/09* (2013.01); *C08L 83/06* (2013.01); *C08L 83/08* (2013.01); *C08G 77/08* (2013.01); *C08G 77/16* (2013.01); *C08G 77/26* (2013.01)

(58) Field of Classification Search
None
See application file for complete search history.

(56) References Cited

U.S. PATENT DOCUMENTS

| | | | |
|---|---|---|---|
| 4,216,140 A | 8/1980 | Simizu | |
| 4,558,109 A | 12/1985 | McAfee | |
| 2004/0092660 A1* | 5/2004 | Koehler et al. | 524/837 |
| 2004/0138373 A1* | 7/2004 | Hamachi et al. | 524/588 |
| 2011/0040063 A1* | 2/2011 | Oishi | C08G 77/12 528/14 |
| 2011/0319557 A1* | 12/2011 | Kojima et al. | 524/588 |

FOREIGN PATENT DOCUMENTS

| | | |
|---|---|---|
| EP | 0 081 119 A1 | 6/1983 |
| EP | 0 106 363 A2 | 4/1984 |
| EP | 0 285 391 A2 | 10/1988 |
| EP | 0 739 928 A2 | 10/1996 |
| JP | S 63-265924 A | 11/1988 |
| JP | H 04-198321 A | 7/1992 |
| JP | 06-092540 B | 11/1994 |
| JP | H 06-092540 B | 11/1994 |
| JP | 3251658 B | 11/2001 |
| WO | WO 2010/074297 A1 | 7/2010 |

OTHER PUBLICATIONS

English language abstract for JPH 04-198321 extracted from PAJ database on Aug. 20, 2014, 1 page.
Machine-Assisted English translation for JPH 06-092540 extracted from the PAJ database on Aug. 20, 2014, 17 pages.
Machine-Assisted English translation for JP 3251658 extracted from the PAJ database on Aug. 20, 2014, 21 pages.
International Search Report for Application No. PCT/JP2012/081870 dated Mar. 13, 2013, 4 pages.
English language abstract for JPS 63-265924 extracted from PAJ database on Aug. 20, 2014, 1 page.

\* cited by examiner

*Primary Examiner* — Susan Tran
(74) *Attorney, Agent, or Firm* — Howard & Howard Attorneys PLLC

(57) ABSTRACT

The present invention relates to a use of an acid in a manufacture of an organopolysiloxane through a condensation reaction of a silicon-containing compound containing a silicon-bonded hydroxyl group and a silicon-containing compound containing a silicon-bonded aminoxy group. Particularly, the present invention relates to a low-odor composition including such an organopolysiloxane. The composition according to the present invention can have little odor caused by a by-product produced via the condensation reaction described above.

11 Claims, No Drawings

USE OF ACID IN THE MANUFACTURE OF ORGANOPOLYSILOXANE

CROSS-REFERENCE TO RELATED APPLICATIONS

This application is the National Stage of International Patent Application No. PCT/JP2012/081870, filed on Dec. 4, 2012, which claims priority to and all the advantages of Japanese Patent Application No. JP2011-275721, filed on Dec. 16, 2011, the content of which is incorporated herein by reference.

TECHNICAL FIELD

The present invention relates to a use of an acid to reduce odor produced in the manufacture of an organopolysiloxane through a condensation reaction of a silicon-containing compound containing a silicon-bonded hydroxyl group and a silicon-containing compound containing a silicon-bonded aminoxy group. Particularly, the present invention relates to a low-odor composition including such an organopolysiloxane.

BACKGROUND ART

Conventionally, manufacturing an organopolysiloxane through a condensation reaction of a silicon-containing compound containing a silicon-bonded hydroxyl group and a silicon-containing compound containing a silicon-bonded aminoxy group is known.

For example, Japanese Examined Patent Application Publication No. H06-092540 describes an organopolysiloxane emulsion comprising an organopolysiloxane having silanol groups at both molecular terminals, a silicon compound having aminoxy groups at both molecular terminals, a nonionic emulsifying agent, and water.

Japanese Unexamined Patent Application Publication No. S63-265924 describes a method for manufacturing an organopolysiloxane emulsion comprising: emulsion polymerizing an organopolysiloxane having silanol groups at both molecular terminals and a silicon compound having aminoxy groups at both molecular terminals in the presence of a surfactant, in water.

Japanese Unexamined Patent Application Publication No. H04-198321 describes a method for manufacturing an organopolysiloxane emulsion comprising: emulsion polymerizing a silicon compound having aminoxy groups at both molecular terminals and an organopolysiloxane having silanol groups at both molecular terminals, from which the non-condensation reacting oligomer component having 20 silicon atoms or less is removed, in the presence of a surfactant, in water.

Japanese Patent No. 3251658 describes a silicone aqueous emulsion composition comprising an organopolysiloxane resin, an organopolysiloxane having silanol groups at both molecular terminals, a silicon compound having aminoxy groups at both molecular terminals, a surfactant, and water.

PRIOR ART DOCUMENTS

Patent Documents

[Patent Document 1] Japanese Examined Patent Application Publication No. H06-092540
[Patent Document 2] Japanese Unexamined Patent Application Publication No. S63-265924
[Patent Document 3] Japanese Unexamined Patent Application Publication No. H04-198321
[Patent Document 4] Japanese Patent No. 3251658

SUMMARY OF INVENTION

Technical Problem

The condensation reaction of a silicon-containing compound containing a silicon-bonded hydroxyl group and a silicon-containing compound containing a silicon-bonded aminoxy group is advantageous in that it can yield an organopolysiloxane having a low content of volatile cyclic polysiloxane and an organopolysiloxane having a high molecular weight can be easily manufactured. However, the odor of hydroxylamine, produced as a by-product of the condensation reaction, is a problem. Particularly, in some cases, it can be difficult to remove the hydroxylamine from a composition using distillation or the like when said composition comprises an organopolysiloxane obtained using the condensation reaction described above, and the odor leads to the possible limitation of applications of said composition.

An object of the present invention is to provide a composition containing an organopolysiloxane manufactured via the condensation reaction described above, and also having little odor.

Additionally, another object of the present invention is to provide an organopolysiloxane that is manufactured via the condensation reaction described above, and also has reduced odor.

Solution to Problem

The object of the present invention are achieved by an organopolysiloxane composition comprising at least one type of an inorganic acid or a carboxylic acid, and also an organopolysiloxane obtained by condensation reacting at least one type of a silicon-containing compound containing a silicon-bonded hydroxyl group and at least one type of a silicon-containing compound containing a silicon-bonded aminoxy group.

The composition of the present invention preferably comprises not less than 0.3 mol of the inorganic acid or the carboxylic acid per 1 mol of the silicon-containing compound containing a silicon-bonded aminoxy group.

The inorganic acid can be selected from the group consisting of hydrochloric acid, sulfuric acid, nitric acid, phosphoric acid, and carbonic acid.

The silicon-containing compound containing a silicon-bonded hydroxyl group is preferably a diorganopolysiloxane capped at both molecular terminals with diorganohydroxysilyl groups.

The silicon-containing compound containing a silicon-bonded aminoxy group is preferably a diorganopolysiloxane capped at both molecular terminals with diorganoaminoxysilyl groups, a diorganosiloxane-polyoxyalkylene block copolymer capped at both molecular terminals with diorganoaminoxysilyl groups, an aminoxyorganopolysiloxane capped at both molecular terminals with triorganosilyl groups, or a diorganosiloxane-aminoxyorganosiloxane copolymer capped at both molecular terminals with triorganosilyl groups.

The silicon-bonded aminoxy group is preferably —ON($R^3$)$_2$ (wherein $R^3$ are each independently a hydrogen atom or a substituted or unsubstituted, straight, branched, or cyclic monovalent hydrocarbon group having from 1 to 30 carbons) or a group represented by the following formula:

In the formula, $R^4$ is an oxygen atom, a sulfur atom, or a divalent organic group.

In the above formula, the divalent organic group $R^4$ moiety is preferably —$N(R^5)$— (wherein $R^5$ is a hydrogen atom or a substituted or unsubstituted, straight, branched, or cyclic monovalent hydrocarbon group having from 1 to 30 carbons); a substituted or unsubstituted, straight or branched divalent hydrocarbon group having from 1 to 20 carbons; or a substituted or unsubstituted, straight or branched divalent hydrocarbon group comprising at least one hetero-atom and having from 1 to 20 carbons.

The composition of the present invention may further comprise a surfactant.

The composition of the present invention may further comprise water.

The composition of the present invention may be in the form of an emulsion.

The composition of the present invention is preferably compounded in a cosmetic composition.

The cosmetic composition is preferably a hair cosmetic composition.

The object of the present invention is also achieved by a method for manufacturing an organopolysiloxane, the method comprising: condensation reacting at least one type of a silicon-containing compound containing a silicon-bonded hydroxyl group and at least one type of a silicon-containing compound containing a silicon-bonded aminoxy group in the presence of at least one type of an inorganic acid or a carboxylic acid.

Additionally, the object of the present invention is also achieved by a method for manufacturing an organopolysiloxane, the method comprising the steps of: obtaining a composition comprising an organopolysiloxane obtained by condensation reacting at least one type of a silicon-containing compound containing a silicon-bonded hydroxyl group and at least one type of a silicon-containing compound containing a silicon-bonded aminoxy group; and adding at least one type of an inorganic acid or a carboxylic acid to said composition.

The organopolysiloxane that is obtainable via the manufacturing methods of the present invention is low-odor.

Advantageous Effects of Invention

The organopolysiloxane composition of the present invention has little odor originating from hydroxylamine. Additionally, the content of volatile cyclic polysiloxane in the organopolysiloxane composition of the present invention is low and, furthermore, the organopolysiloxane composition of the present invention can comprise an organopolysiloxane having a high molecular weight. Thus, the organopolysiloxane composition of the present invention can be suitably used in cosmetic composition applications.

In the methods for manufacturing an organopolysiloxane of the present invention, an organopolysiloxane with low odor can be obtained regardless of a silicon-containing compound containing a silicon-bonded hydroxyl group and a silicon-containing compound containing a silicon-bonded aminoxy group being condensation reacted. Moreover, with the methods for manufacturing an organopolysiloxane of the present invention, an organopolysiloxane having a low content of volatile cyclic polysiloxane and having a high molecular weight can be easily manufactured. Thus, the organopolysiloxane obtained via the manufacturing methods of the present invention can be suitably used in cosmetic composition applications.

DESCRIPTION OF EMBODIMENTS

An organopolysiloxane composition of the present invention comprises an organopolysiloxane obtained by condensation reacting (A) at least one type of a silicon-containing compound containing a silicon-bonded hydroxyl group and (B) at least one type of a silicon-containing compound containing a silicon-bonded aminoxy group, and also (C) at least one type of an inorganic acid or a carboxylic acid. First, descriptions of these, components (A), (B), and (C), will be given below.

Component (A)

The silicon-containing compound containing a silicon-bonded hydroxyl group is not particularly limited, provided that it contains a silicon-bonded hydroxyl group, but is preferably a diorganopolysiloxane capped at both molecular terminals with diorganohydroxysilyl groups. A viscosity of the component (A) is not particularly limited, but is preferably in a range from 1 to 100,000 $mm^2/s$. A single type of the component (A) may be used, or a combination of two or more types may be used.

The diorganopolysiloxane capped at both molecular terminals with diorganohydroxysilyl groups is preferably an organopolysiloxane represented by the general formula:

$$HO(R^1{}_2SiO)_mH$$

In the formula, $R^1$ are each independently a substituted or unsubstituted, straight, branched, or cyclic monovalent hydrocarbon group having from 1 to 30 carbons; and m is an integer of not less than 10, is preferably an integer in a range from 10 to 1,000, and is more preferably an integer in a range from 100 to 500.

The substituted or unsubstituted, straight, branched, or cyclic monovalent hydrocarbon group having from 1 to 30 carbons, for example, is a monovalent saturated hydrocarbon group having preferably from 1 to 20 carbons, more preferably from 1 to 10 carbons, and even more preferably from 1 to 4 carbons; a monovalent unsaturated aliphatic hydrocarbon group having preferably from 2 to 20 carbons, more preferably from 2 to 10 carbons, and even more preferably from 2 to 4 carbons; or a monovalent aromatic hydrocarbon group having preferably from 6 to 20 carbons, more preferably from 6 to 12 carbons, and even more preferably from 6 to 8 carbons.

Examples of the monovalent saturated hydrocarbon group include straight or branched alkyl groups such as methyl groups, ethyl groups, n-propyl groups, isopropyl groups, n-butyl groups, isobutyl groups, sec-butyl groups, tert-butyl groups, pentyl groups, hexyl groups, heptyl groups, octyl groups, nonyl groups, decyl groups, and the like; and cycloalkyl groups such as cyclopentyl groups, cyclohexyl groups, cycloheptyl groups, cyclooctyl groups, and the like. Of these, a straight or branched alkyl group having from 1 to 4 carbons is preferable and a methyl group is particularly preferable.

Examples of the monovalent unsaturated aliphatic hydrocarbon group include straight or branched alkenyl groups such as vinyl groups, 1-propenyl groups, allyl groups, isopropenyl groups, 1-butenyl groups, 2-butenyl groups, pentenyl groups, hexenyl groups, and the like; cycloalkenyl groups such as cyclopentenyl groups, cyclohexenyl groups, and the like; and, furthermore, cycloalkenylalkyl groups such as cyclopentenylethyl groups, cyclohexenylethyl groups, cyclohexenylpropyl groups, and the like. Of these, a straight or branched alkenyl group is preferable and a vinyl group is particularly preferable.

Examples of the monovalent aromatic hydrocarbon group include aryl groups such as phenyl groups, tolyl groups, xylyl groups, mesityl groups, and the like. Of these, a phenyl group is preferable. Note that in the present specification, "aromatic hydrocarbon group" includes groups in which an aromatic hydrocarbon and a saturated hydrocarbon are conjugated in addition to groups formed only from an aromatic hydrocarbon. Examples of groups in which an aromatic hydrocarbon and a saturated hydrocarbon are conjugated include aralkyl groups such as benzyl groups, phenethyl groups, and the like.

The hydrogen atom on the monovalent hydrocarbon group described above may be substituted by one or more substituents, and said substituent may, for example, be a halogen atom (i.e. a fluorine atom, a chlorine atom, a bromine atom, and an iodine atom); a reactive functional group selected from the group consisting of mercapto groups, epoxy groups, amino groups, amide groups, ester groups, (meth)acryloxy groups, and isocyanate groups; or a monovalent hydrocarbon group having said reactive functional group. Examples of the substituted monovalent hydrocarbon group include 3,3,3-trifluoropropyl groups, 3-chloropropyl groups, 3-mercaptopropyl groups, 2,3-epoxypropyl groups, 3,4-epoxybutyl groups, 4,5-epoxypentyl groups, 2-glycidoxyethyl groups, 3-glycidoxypropyl groups, 4-glycidoxybutyl groups, 2-(3,4-epoxycyclohexyl)ethyl groups, 3-(3,4-epoxycyclohexyl)propyl groups, aminopropyl groups, N-methylaminopropyl groups, N-butylaminopropyl groups, N,N-dibutylaminopropyl groups, 3-(2-aminoethoxy)propyl groups, 3-(2-aminoethylamino)propyl groups, 3-carboxypropyl groups, 10-carboxydecyl groups, acryloxypropyl groups, methacryloxypropyl groups, 3-isocyanate propyl groups, and the like. Note that a reactive functional group having an acidic group such as a carboxyl group, a carbinol group, or the like, or an alcoholic hydroxy group is not preferable as the substituent because such a reactive functional group is reactive with respect to the aminoxy group in the component (B).

Specific examples of the diorganopolysiloxane capped at both molecular terminals with diorganohydroxysilyl groups include:

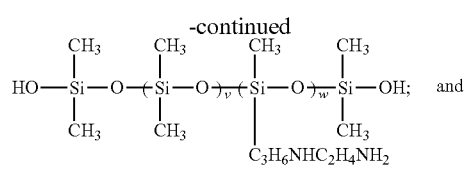

(wherin $s$ is an interger from 8 to 1,000)

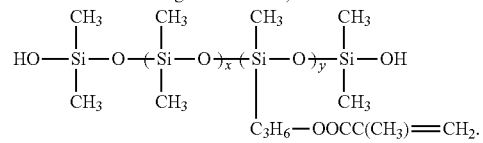

(wherin $t$ is an interger from 7 to 1,000 and $u$ is an integer from 1 to 2)

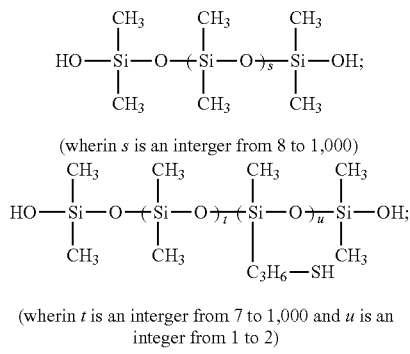

(wherin $v$ is an interger from 7 to 1,000 and $w$ is an integer from 1 to 2)

(wherin $x$ is an interger from 7 to 1,000 and $y$ is an integer from 1 to 2)

Component (B)

The silicon-containing compound containing a silicon-bonded aminoxy group is not particularly limited, provided that it contains a silicon-bonded aminoxy group, but is preferably a diorganopolysiloxane capped at both molecular terminals with diorganoaminoxysilyl groups, a diorganosiloxane-polyoxyalkylene block copolymer capped at both molecular terminals with diorganoaminoxysilyl groups, an aminoxyorganopolysiloxane capped at both molecular terminals with triorganosilyl groups, or a diorganosiloxane-aminoxyorganosiloxane copolymer capped at both molecular terminals with triorganosilyl groups; and more preferably a diorganopolysiloxane capped at both molecular terminals with diorganoaminoxysilyl groups or a diorganosiloxane-polyoxyalkylene block copolymer capped at both molecular terminals with diorganoaminoxysilyl groups. A viscosity of the component (B) is not particularly limited, but is preferably in a range from 1 to 100,000 mm²/s. A single type of the component (B) may be used, or a combination of two or more types may be used.

The diorganopolysiloxane capped at both molecular terminals with diorganoaminoxysilyl groups is preferably an organopolysiloxane represented by the general formula:

D-(R²₂SiO)ₙSiR²₂-D

In the formula, $R^2$ are each independently a substituted or unsubstituted, straight, branched, or cyclic monovalent hydrocarbon group having from 1 to 30 carbons;

D is an aminoxy group; and n is an integer of not less than 1, is preferably an integer in a range from 2 to 1,000, and is more preferably an integer in a range from 3 to 200.

The definition and specific examples of the $R^2$ moiety as a substituted or unsubstituted, straight, branched, or cyclic monovalent hydrocarbon group having from 1 to 30 carbons are as described above.

The silicon-bonded aminoxy group (D in the general formula above) are each independently preferably —ON(R³)₂ (wherein $R^3$ are each independently a hydrogen atom or a substituted or unsubstituted, straight, branched, or cyclic monovalent hydrocarbon group having from 1 to 30 carbons) or a group represented by the following formula:

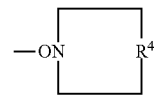

In the formula, $R^4$ is an oxygen atom, a sulfur atom, or a divalent organic group.

The definition and specific examples of the $R^3$ moiety as a substituted or unsubstituted, straight, branched, or cyclic monovalent hydrocarbon group having from 1 to 30 carbons are as described above.

The divalent organic group is not particularly limited, but is preferably —N($R^5$)— (wherein $R^5$ is a hydrogen atom or a substituted or unsubstituted, straight, branched, or cyclic monovalent hydrocarbon group having from 1 to 30 carbons); a substituted or unsubstituted, straight or branched divalent hydrocarbon group having from 1 to 20 carbons; or a substituted or unsubstituted, straight or branched divalent hydrocarbon group comprising at least one hetero-atom and having from 1 to 20 carbons.

The definition and specific examples of the $R^5$ moiety as a substituted or unsubstituted, straight, branched, or cyclic monovalent hydrocarbon group having from 1 to 30 carbons are as described above.

Examples of the substituted or unsubstituted, straight or branched divalent hydrocarbon group having from 1 to 20 carbons include methylene groups, dimethylene groups, trimethylene groups, tetramethylene groups, pentamethylene groups, hexamethylene groups, heptamethylene groups, octamethylene groups, and similar straight or branched alkylene groups having from 1 to 20 carbons; vinylene groups, allylene groups, butenylene groups, hexenylene groups, octenylene groups, and similar alkenylene groups having from 2 to 15 carbons; phenylene groups, diphenylene groups, and similar arylene groups having from 6 to 20 carbons; dimethylenephenylene groups and similar alkylene-arylene groups having from 7 to 20 carbons; and groups wherein the hydrogen atoms bonded to the carbon atoms of these groups are substituted at least partially by fluorine or a similar halogen atom. The divalent hydrocarbon group is preferably a straight or branched alkylene group having from 1 to 20 carbons.

The substituted or unsubstituted, straight or branched divalent hydrocarbon group comprising at least one hetero-atom and having from 1 to 20 carbons is not particularly limited provided that it comprises at least one hetero-atom such as an oxygen atom, a sulfur atom, a nitrogen atom, or the like, but preferably has a molecular skeleton formed from 3 to 17 carbon atoms, and 1 to 3 nitrogen atoms or 1 to 2 oxygen atoms. Examples thereof include —R—O—, —R—O—R'—, —R—CO—, —R—COO—, —R—COO—R'—, —R—CONH—, and —CH=N—R— (wherein R and R' are each independently a substituted or unsubstituted, straight or branched divalent hydrocarbon group having from 1 to 20 carbons). A divalent hydrocarbon group having formula of —CH=N—CH=CH— or —(CH$_2$)$_2$—O—(CH$_2$)$_2$— is particularly preferable.

Specific examples of the diorganopolysiloxane capped at both molecular terminals with diorganoaminoxysilyl groups include:

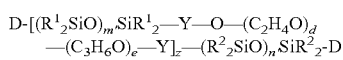

(wherein $a$ is an integer from 1 to 1,000)

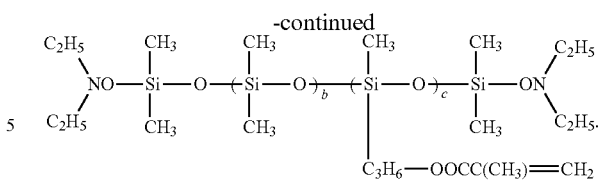

(wherein $b$ is an integer from 1 to 1,000 and $c$ is an integer from 1 to 2)

The diorganosiloxane-polyoxyalkylene block copolymer capped at both molecular terminals with diorganoaminoxysilyl groups is preferably a copolymer represented by the following general formula:

$$D\text{-}[(R^1{}_2SiO)_{m'}SiR^1{}_2\text{—}Y\text{—}O\text{—}(C_2H_4O)_d\text{—}(C_3H_6O)_e\text{—}Y]_z\text{—}(R^2{}_2SiO)_{n'}SiR^2{}_2\text{-}D$$

In this formula, $R^1$, $R^2$ and D are the same as described above;

z is an integer of not less than 1, is preferably an integer in a range from 1 to 10, and is more preferably an integer in a range from 1 to 5;

m' and n' are each independently an integer of not less than 0, preferably an integer in a range from 1 to 10,000, and more preferably an integer in a range from 100 to 3,000, however m'+n' is in a range from 1 to 10,000;

Y is a divalent organic group;

d is an integer of not less than 0, is preferably an integer in a range from 0 to 1,000, and is more preferably an integer in a range from 10 to 300;

e is an integer of not less than 0, is preferably an integer in a range from 0 to 100, and is more preferably an integer in a range from 0 to 10; and d+e is preferably at least 2, more preferably not less than 4, even more preferably in a range from 10 to 500, and yet even more preferably in a range from 10 to 300. Here, the definition and specific examples of the divalent organic group are as described above. Note that Y is preferably bonded to an adjacent silicon atom via a carbon-silicon bond, and is preferably bonded to a polyoxyalkylene block (—(C$_2$H$_4$O)$_d$—(C$_3$H$_6$O)$_e$—) via an adjacent oxygen atom.

A content of the polyoxyalkylene block in the block copolymer is preferably from 10 to 95 wt %, more preferably from 20 to 85 wt %, and even more preferably from 40 to 85 wt %. Additionally, preferably not less than 60 wt % and more preferably not less than 70 wt % of the polyoxyalkylene block is constituted by polyoxyethylene groups. Note that a weight average molecular weight of the polyoxyalkylene block is preferably from 200 to 15,000.

Component (C)

The inorganic acid or the carboxylic acid is not particularly limited but is preferably an acid that is soluble in water, and is more preferably an Arrhenius acid, which emits protons into an aqueous solution. A single type of inorganic acid and carboxylic acid may be used, a mixture of two or more types of the inorganic acid may be used, or a mixture of two or more types of the carboxylic acid may be used. Note that a mixture of the inorganic acid and the carboxylic acid can also be used.

The inorganic acid is not particularly limited, and examples thereof include hydrochloric acid, sulfuric acid, nitric acid, phosphoric acid, carbonic acid, boric acid, and the like.

In the present specification, "phosphoric acid" includes alkyl phosphoric acid, and "sulfuric acid" includes alkyl sulfuric acid.

The carboxylic acid is not particularly limited, and can be a monocarboxylic acid (including monohydroxy monocarboxylic acid and dihydroxy monocarboxylic acid), a dicarboxylic acid (including monohydroxy dicarboxylic acid and dihydroxy dicarboxylic acid), a polycarboxylic acid, or the like. Examples thereof include:

Straight saturated aliphatic monocarboxylic acids (alkanoic acids) such as formic acid, acetic acid, propionic acid, butyric acid, valeric acid, caproic acid, enanthic acid, caprylic acid, pelargonic acid, capric acid, undecanoic acid, and the like;

Branched saturated aliphatic monocarboxylic acids (alkanoic acids) such as 2-methylpropanoic acid, 2-methylbutanoic acid, trimethylpropanoic acid, 2-methylpentanoic acid, trimethyl acetic acid, and the like;

Unsaturated aliphatic monocarboxylic acids (alkenoic acids) such as acrylic acid, methacrylic acid, crotonic acid, isocrotonic acid, vinyl acetic acid, allyl acetic acid, hexenoic acid, heptenoic acid, octenoic acid, and the like;

Unsaturated aliphatic monocarboxylic acids (alkynoic acids) such as propiolic acid, tetrolic acid, allyl acetic acid, hexynoic acid, octynoic acid, and the like;

Polyunsaturated aliphatic monocarboxylic acids such as pentadienoic acid, sorbic acid, and the like;

α-hydroxymonocarboxylic acids such as citric acid, lactic acid, glycolic acid, α-oxybutyric acid, and the like;

β-hydroxymonocarboxylic acids such as 2-hydroxyvaleric acid, 2-hydroxycaproic acid, β-oxybutyric acid, and the like;

γ-hydroxymonocarboxylic acids such as γ-oxybutyric acid and the like;

Dihydroxymonocarboxylic acids such as glyceric acid and the like;

Other hydroxymonocarboxylic acids such as hydroxy(meth)acrylic acid and the like;

Saturated aliphatic dicarboxylic acids such as oxalic acid, malonic acid, succinic acid, glutaric acid, adipic acid, and the like;

Monohydroxy saturated aliphatic dicarboxylic acids such as tartronic acid, malic acid, and the like;

Dihydroxy saturated aliphatic dicarboxylic acids such as tartaric acid and the like;

Unsaturated aliphatic dicarboxylic acids such as maleic acid, fumaric acid, and the like;

Aromatic monocarboxylic acid such as benzoic acid and the like;

Aromatic dicarboxylic acids such as phthalic acid and the like;

Amino acids such as glycine, alanine, valine, leucine, glutamic acid, aspartic acid, PL-pyrrolidone carboxylic acid, and the like; and Polycarboxylic acids such as gallic acid and the like.

Next, the organopolysiloxane composition of the present invention will be further described.

In the present invention, condensation reacting at least one type of the component (A) and at least one type of the component (B) results in an organopolysiloxane. The organopolysiloxane composition of the present invention can be manufactured using arbitrary conditions because the condensation reaction of the component (A) with the component (B) is carried out easily. For example, an organopolysiloxane is produced via a condensation reaction of the component (A) and the component (B) by simply adding and mixing the component (A) and the component (B) in a reaction system including the component (C). Therefore, a composition including the component (C) in conjunction with the organopolysiloxane can be obtained. The order in which the component (A) and the component (B) are added to the reaction system can be selected as desired and the component (A) may be added first or the component (B) may be added first. On the other hand, the component (B) may be added and mixed with a reaction system including the component (A) and the component (C) or, alternately, the component (A) may be added and mixed with a reaction system including the component (B) and the component (C). Furthermore, the component (C) may be added and mixed with a reaction system including the component (A) and the component (B). The condensation reaction of the component (A) and the component (B) begins quickly after a state in which both components are present in the same reaction system, but the reaction system is preferably agitated so that the reaction is carried out uniformly. Additionally, a reaction temperature and reaction time of the condensation reaction are not particularly limited and, for example, the reaction can be sufficiently carried out by agitating or allowing the reaction system to sit at rest at room temperature for a number of days.

Usage amounts of the component (A) and the component (B) in the organopolysiloxane composition of the present invention can be selected as desired and, for example, from 0.01 to 10,000 parts by weight, preferably from 0.1 to 100 parts by weight, and more preferably from 1 to 10 parts by weight of the component (B) can be used per 100 parts by weight of the component (A). However, in order to reduce the amount of unreacted reactant, a relative amount of the silicon-bonded aminoxy group, preferably in a range from 0.8 to 10 mol and more preferably in a range from 0.9 to 5 mol per 1 mol of the silicon-bonded hydroxyl group is used.

A usage amount of the component (C) can be selected as desired and, for example, from 0.001 to 10 parts by weight, preferably from 0.01 to 5 parts by weight, and more preferably from 0.1 to 1 parts by weight of the component (C) can be used per 100 parts by weight of the component (A). Additionally, from 0.01 to 100 parts by weight, preferably from 0.1 to 50 parts by weight, and more preferably from 1 to 20 parts by weight of the component (C) may be used per 100 parts by weight of the component (B). However, in order to effectively reduce odor of the hydroxylamine that is produced as a by-product of the condensation reaction, preferably not less than 0.3 mol, more preferably not less than 0.5 mol, and even more preferably not less than 1 mol of the component (C) is used per 1 mol of the component (B).

The molecular weight of the organopolysiloxane obtained via the condensation reaction of the component (A) and the component (B) is large, and, for example, can have a weight average molecular weight from 10,000 to 3,000,000, preferably from 50,000 to 1,500,000, more preferably from 90,000 to 1,000,000, and even more preferably from 100,000 to 600,000. It is preferable that the weight average molecular weight is not less than 5,000. Additionally, the organopolysiloxane can have a viscosity that is from 100,000 to 8,000,000 mm$^2$/s, and preferably has a viscosity that is in a range from 200,000 to 6,000,000 mm$^2$/s.

Thus, the organopolysiloxane obtained via the present invention has a high molecular weight and, therefore, the organopolysiloxane composition of the present invention including said organopolysiloxane can, for example, exhibit superior properties as a raw material for use in cosmetic compositions.

Additionally, with the present invention, an amount of low molecular weight cyclic siloxanes such as octamethylcyclotetrasiloxane, decamethylcyclopentasiloxane, dodecamethylcyclohexasiloxane, and the like, which is a by-product of the condensation reaction of the component (A) and the component (B) is small. These low molecular weight cyclic siloxanes are volatile and, particularly when combined with a film forming polymer and applied to the skin, discomfort such as a sense of dryness may occur. However, the content of such volatile cyclic polysiloxanes is low in the organopolysiloxane composition of the present invention and, therefore, from the perspective of sensation during use as well, the organopolysiloxane composition of the present invention is suitable as a raw material for use in cosmetic compositions.

Regardless of being obtained via the condensation reaction of the silicon-containing compound containing a silicon-bonded hydroxyl group and the silicon-containing compound containing a silicon-bonded aminoxy group, with the organopolysiloxane obtained through the present invention, odor originating from the hydroxylamine that is inevitably produced as a by-product of said condensation reaction is reduced. Therefore, from the perspective of odor as well, the organopolysiloxane composition of the present invention is suitable as a raw material for use in cosmetic compositions.

The organopolysiloxane composition of the present invention can further comprise a surfactant. The surfactant is not particularly limited, and at least one type can be selected from the group consisting of anionic surfactants, cationic surfactants, nonionic surfactants, amphoteric surfactants, and semipolar surfactants.

Examples of the anionic surfactants include saturated or unsaturated fatty acid salts (e.g. sodium laurate, sodium stearate, sodium oleate, sodium linolenate, and the like); alkylsulfuric acid salts; alkylbenzene sulfonic acids (e.g. hexylbenzenesulfonic acid, octylbenzenesulfonic acid, dodecylbenzenesulfonic acid, and the like) and salts thereof; polyoxyalkylene alkyl ether sulfuric acid salts; polyoxyalkylene alkenyl ether sulfuric acid salts; polyoxyethylene alkylsulfuric ester salts; sulfosuccinic acid alkyl ester salts; polyoxyalkylene sulfosuccinic acid alkyl ester salts; polyoxyalkylene alkylphenyl ether sulfuric acid salts; alkanesulfonic acid salts; octyltrimethylammonium hydroxide; dodecyltrimethylammonium hydroxide; alkyl sulfonates; polyoxyethylene alkylphenyl ether sulfuric acid salts; polyoxyalkylene alkyl ether acetic acid salts; alkyl phosphoric acid salts; polyoxyalkylene alkyl ether phosphoric acid salts; acylglutamic acid salts; α-acylsulfonic acid salts; alkylsulfonic acid salts; alkylallylsulfonic acid salts; α-olefinsulfonic acid salts; alkylnaphthalene sulfonic acid salts; alkanesulfonic acid salts; alkyl- or alkenylsulfuric acid salts; alkylamide sulfuric acid salts; alkyl- or alkenyl phosphoric acid salts; alkylamide phosphoric acid salts; alkyloylalkyl taurine salts; N-acylamino acid salts; sulfosuccinic acid salts; alkyl ether carboxylic acid salts; amide ether carboxylic acid salts; α-sulfofatty acid ester salts; alanine derivatives; glycine derivatives; and arginine derivatives. Examples of salts include alkali metal salts such as sodium salts and the like, alkaline earth metal salts such as magnesium salts and the like, alkanolamine salts such as triethanolamine salts and the like, and ammonium salts.

Examples of cationic surfactants include alkyltrimethylammonium chloride, stearyltrimethylammonium chloride, lauryltrimethylammonium chloride, cetyltrimethylammonium chloride, beef tallow alkyltrimethylammonium chloride, behenyltrimethylammonium chloride, stearyltrimethylammonium bromide, behenyltrimethylammonium bromide, distearyldimethylammonium bromide, dicocoyldimethylammonium chloride, dioctyldimethylammonium chloride, di(POE)oleylmethylammonium (2 EO) chloride, benzalkonium chloride, alkyl benzalkonium chloride, alkyl dimethylbenzalkonium chloride, benzethonium chloride, stearyl dimethylbenzylammonium chloride, lanolin derivative quaternary ammonium salt, diethylaminoethylamide stearate, dimethylaminopropylamide stearate, behenic acid amide propyldimethyl hydroxypropylammonium chloride, stearoyl colaminoformyl methylpyridinium chloride, cetylpyridinium chloride, tall oil alkylbenzyl hydroxyethylimidazolinium chloride, and benzylammonium salt.

Examples of nonionic surfactants include polyoxyalkylene ethers, polyoxyalkylene alkyl ethers, polyoxyalkylene fatty acid esters, polyoxyalkylene fatty acid diesters, polyoxyalkylene resin acid esters, polyoxyalkylene (hydrogenated) castor oils, polyoxyalkylene alkyl phenols, polyoxyalkylene alkyl phenyl ethers, polyoxyalkylene phenyl phenyl ethers, polyoxyalkylene alkyl esters, polyoxyalkylene alkyl esters, sorbitan fatty acid esters, polyoxyalkylene sorbitan alkyl esters, polyoxyalkylene sorbitan fatty acid esters, polyoxyalkylene sorbitol fatty acid esters, polyoxyalkylene glycerol fatty acid esters, polyglycerol alkyl ethers, polyglycerol fatty acid esters, sucrose fatty acid esters, fatty acid alkanolamides, alkylglucosides, polyoxyalkylene fatty acid bisphenyl ethers, polypropylene glycol, diethyleneglycol, polyoxyalkylene-modified silicones, polyglyceryl-modified silicones, glyceryl-modified silicones, sugar-modified silicones, fluorine-based surfactants, polyoxyethylene/polyoxypropylene block polymers, and alkyl polyoxyethylene/polyoxypropylene block polymer ethers. Additionally, as necessary, polyoxyalkylene-modified silicones, polyglyceryl-modified silicones, and glyceryl-modified silicones in which an alkyl branch, a straight chain silicone branch, a siloxane dendrimer branch, or the like is provided with the hydrophilic group can be suitably used.

Examples of amphoteric surfactants include imidazoline-type, amidobetaine-type, alkylbetaine-type, alkylamidobetaine-type, alkylsulfobetaine-type, amidosulfobetaine-type, hydroxysulfobetaine-type, carbobetaine-type, phosphobetaine-type, aminocarboxylic acid-type, and amidoamino acid-type amphoteric surfactants. Specifically, imidazoline-type amphoteric surfactants such as 2-undecyl-N,N,N-(hydroxyethylcarboxymethyl)-2-imidazoline sodium, 2-cocoyl-2-imidazolinium hydroxide-1-carboxyethyloxy disodium salt, and the like; alkylbetaine-type amphoteric surfactants such as lauryl dimethylaminoacetic betaine, myristyl betaine, and the like; amidobetaine-type amphoteric surfactants such as coconut oil fatty acid amidopropyl dimethylamino acetic acid betaine, palm kernel oil fatty acid amidopropyl dimethylamino acetic acid betaine, beef tallow fatty acid amidopropyl dimethylamino acetic acid betaine, hardened beef tallow fatty acid amidopropyl dimethylamino acetic acid betaine, lauric acid amidopropyl dimethylamino acetic acid betaine, myristic acid amidopropyl dimethylamino acetic acid betaine, palmitic acid amidopropyl dimethylamino acetic acid betaine, stearic acid amidopropyl dimethylamino acetic acid betaine, oleic acid amidopropyl dimethylamino acetic acid betaine, and the like; alkylsulfobetaine-type amphoteric surfactants such as coconut oil fatty acid dimethyl sulfopropyl betaine and the like; alkyl hydroxy sulfobetaine-type amphoteric surfactants such as lauryl dimethylaminohydroxy sulfobetaine and the like; phosphobetaine-type amphoteric surfactants such as laurylhydroxy phosphobetaine and the like; and amidoamino acid-type amphoteric surfactants such as sodium N-lauroyl-N'-hydroxyethyl-N'-carboxymethyl ethylenediamine, sodium N-oleoyl-N'-hydroxyethyl-N'-carboxymethyl ethylenediamine, sodium N-cocoyl-N'-hydroxyethyl-N'-carboxymethyl ethylenediamine, potassium N-lauroyl-N'-hydroxyethyl-N'-carboxymethyl ethylenediamine, potassium N-oleoyl-N'-hydroxyethyl-N'-carboxymethyl ethylenediamine, sodium N-lauroyl-N-hydroxyethyl-N'-carboxymethyl ethylenediamine, sodium N-oleoyl-N-hydroxyethyl-N'-carboxymethyl ethylenediamine, sodium N-cocoyl-N-hydroxyethyl-N'-carboxymethyl ethylenediamine, monosodium N-lauroyl-N-hydroxyethyl-N',N'-dicarboxymethyl ethylenediamine, monosodium N-oleoyl-N-hydroxyethyl-N',N'-dicarboxymethyl ethylenediamine, monosodium N-cocoyl-N-hydroxyethyl-N',N'-dicarboxymethyl ethylenediamine, disodium N-lauroyl-N-hydroxyethyl-N',N'-dicarboxymethyl ethylenediamine, disodium N-oleoyl-N-hydroxyethyl-N',N'-dicarboxymethyl ethylenediamine, disodium N-cocoyl-N-hydroxyethyl-N',N'-dicarboxymethyl ethylenediamine, and the like.

Examples of semipolar surfactants include alkylamine oxide-type surfactants, alkylamine oxides, alkylamide amine oxides, alkylhydroxyamine oxides, and the like. Alkyldimethylamine oxides having from 10 to 18 carbons, alkoxyethyl dihydroxyethylamine oxides having from 8 to 18 carbons, and the like are preferably used. Specific examples thereof include dodecyldimethylamine oxide, dimethyloctylamine oxide, diethyldecylamine oxide, bis-(2-hydroxyethyl)dodecylamine oxide, dipropyltetradecylamine oxide, methylethylhexadecylamine oxide, dodecylamidopropyldimethylamine oxide, cetyldimethylamine oxide, stearyldimethylamine oxide, tallow dimethylamine oxide, dimethyl-2-hydroxyoctadecylamine oxide, lauryldimethylamine oxide, myristyldimethylamine oxide, stearyldimethylamine oxide, isostearyldimethylamine oxide, coconut fatty acid alkyldimethylamine oxide, caprylic amide propyldimethylamine oxide, capric amide propyldimethylamine oxide, lauric amide propyldimethylamine oxide, myristic amide propyldimethylamine oxide, palmitic amide propyldimethylamine oxide, stearic amide propyldimethylamine oxide, isostearic amide propyldimethylamine oxide, oleic amide propyldimethylamine oxide, ricinoleic amide propyldimethylamine oxide, 12-hydroxystearic amide propyldimethylamine oxide, coconut fatty acid amide propyldimethylamine oxide, palm kernel oil fatty acid amide propyldimethylamine oxide, castor oil fatty acid amide propyldimethylamine oxide, lauric amide ethyldimethylamine oxide, myristic amide ethyldimethylamine oxide, coconut fatty acid amide ethyldimethylamine oxide, lauric amide ethyldiethylamine oxide, myristic amide ethyldiethylamine oxide, coconut fatty acid amide ethyldiethylamine oxide, lauric amide ethyldihydroxyethylamine oxide, myristic amide ethyldihydroxyethylamine oxide, and coconut fatty acid amide ethyldihydroxyethylamine oxide.

A content of the surfactant in the organopolysiloxane composition of the present invention is not particularly limited and, for example, a range from 0.1 to 50 wt. % (mass %) and preferably a range from 1 to 20 wt. % (mass %) based on the total weight (mass) of the composition can be compounded.

The organopolysiloxane composition of the present invention can further comprise water. A content of the water is not particularly limited and, for example, a proportion from 10 to 1,000 parts by weight, preferably from 30 to 500 parts by weight, and more preferably from 50 to 300 parts by weight of the water per 100 parts by weight of the component (A) can be used.

In cases where the organopolysiloxane composition of the present invention includes the water and the surfactant, it is possible to perform the condensation reaction of the component (A) and the component (B) as an emulsion polymerization in said composition. The emulsion polymerization can be performed using a conventionally known method. For example, the emulsion polymerization can be performed by uniformly mixing the component (A), the component (B), the surfactant, and the water; thereafter stirring and emulsifying the mixture using an emulsifier such as a colloid mill, a line mill, a homomixer, or the like; and then adding water and uniformly stirring/dispersing the emulsion therein. As necessary, the emulsion may be further stabilized by stirring/emulsifying using an emulsifier such as a homogenizer or the like. It is not necessary to heat the composition because the condensation reaction of the component (A) and the component (B) proceeds at room temperature. However, if necessary, the composition may be heated to a temperature of, for example, 50 to 70° C. As a result, the reaction can be completed in 30 minutes to 12 hours. In this case, the organopolysiloxane composition of the present invention can be configured to be in an emulsion state, and can be used as-is as a raw material in emulsion-state cosmetic compositions.

Odor originating from hydroxylamine is low because the component (C) is present in the organopolysiloxane composition of the present invention along with the elongated chain organopolysiloxane obtained through the condensation reaction of the component (A) and the component (B). Therefore, the composition of the present invention can be a low-odor organopolysiloxane composition. Moreover, the content of volatile cyclic polysiloxanes is low and, furthermore, the organopolysiloxane having a high molecular weight can be included in the organopolysiloxane composition of the present invention. Therefore, the organopolysiloxane composition of the present invention can be suitably used in cosmetic composition applications.

The organopolysiloxane composition of the present invention can optionally comprise a reaction medium other than water such as a solvent, a dispersing medium, or the like. Use of a reaction medium is not necessary but, for example, in cases where the viscosity of the obtained composition is excessively high or, alternately, in cases where it is necessary to increase the dispersibility of the components, a reaction medium such as an inert solvent, a dispersing medium, or the like is preferably used in the reaction. The inert reaction medium preferably does not have a hydroxyl group, and examples of such reaction media include low viscosity polysiloxanes, aliphatic hydrocarbons, aromatic hydrocarbons, ester oils, and the like that do not have a hydroxyl group.

The organopolysiloxane composition of the present invention can be compounded in cosmetic compositions as a low-odor raw material for use in cosmetic compositions. A compounded amount thereof is not particularly limited and, for example, can be in a range from 1 to 99 wt %, 10 to 90 wt %, or 20 to 80 wt %, based on the total weight (mass) of the cosmetic composition.

In addition to the composition described above, the cosmetic composition of the present invention can comprise other optional components. Examples of the optional components include oil agents, surfactants, water-soluble polymers, alcohols, thickening agents/gelling agents, powders, solid silicone resins or crosslinking organopolysiloxanes, acryl silicone dendrimer copolymers, ultraviolet light blocking components, oxidation hair colorants, direct dyes, moisturizing agents, preservatives, antimicrobial agents, perfumes, salts, oxidizing agents or antioxidants, chelating agents, refreshing agents, anti-inflammatory agents, and bioactive components (e.g. skin-lightening agents, cell activating agents, skin trouble improvers, circulation promoters, skin astringents, antiseborrheic agents, vitamins, amino acids, nucleic acids, hormones, and the like).

The type of cosmetic composition is not particularly limited, and specific examples of products include skin cosmetic composition products such as skin cleansing products, skin care cosmetic composition products, makeup cosmetic composition products, anti-perspirants, UV screening products, and the like; hair cosmetic composition products such as hair cleansing products, hair dressing products, hair coloring products, hair growth products, hair treatment products, and the like; and bath use products. Particularly, the cosmetic composition of the present invention comprises an organopolysiloxane having a high molecular weight and, therefore, is suitable as a hair cosmetic composition.

Specific examples of hair cosmetic compositions include shampoos, rinse-in shampoos, and similar hair cleansing agents; hair oils, hair waxes, hair use curl holding agents, setting agents, hair creams, hairsprays, hair liquids, and similar hair dressing products; hair coloring substances, temporary dyes, permanent dyes, and similar hair coloring products; hair tonics, hair treatment essences, hair packs, and similar hair growth products; hair rinses, hair conditioners, and similar hair treatment products.

The form of the cosmetic composition of the present invention is not particularly limited, and the cosmetic composition may be used in a W/O emulsion, O/W emulsion, liquid, solid, paste-like, gel-like, mousse-like, mist-like, granule, or similar form. Of these, the O/W emulsion form is preferable.

On the other hand, a film that is releasable, peelable, water repellent, stain repellent, and weather resistant can be formed by applying the organopolysiloxane composition of the present invention to an arbitrary substrate via a method such as spraying, rolling, brushing, immersing, or the like and, thereafter, allowing the substrate to sit at rest or heat drying the substrate. Therefore, the organopolysiloxane composition of the present invention can also be used as a mold release agent, a release agent for rubber product, a coating agent for release paper, a fabric coating agent, an aqueous paint, a fiber treatment agent, or the like.

In this case, the organopolysiloxane composition of the present invention can, as necessary, comprise an organic carboxylate of a metal such as iron, lead, antimony, cadmium, titanium, calcium, bismuth, zirconium, and the like; an organic amine compound such as triethanolamine, triethylenediamine, dimethylphenylamine, and the like; a preservative; a colorant; a resin processing agent such as glyoxal resin, melanin resin, urea resin, polyester resin, acrylic resin, and the like; a rubber latex such as a styrene-butadiene latex, a natural rubber, or the like; an emulsion of a fluororesin; an emulsion of an organohydrogenpolysiloxane; an emulsion of an organoalkoxysilane; and the like.

The present invention also relates to a method for manufacturing a low-odor organopolysiloxane, the method comprising: condensation reacting at least one type of a silicon-containing compound containing a silicon-bonded hydroxyl group and at least one type of a silicon-containing compound containing a silicon-bonded aminoxy group in the presence of at least one type of an inorganic acid or a carboxylic acid. In this manufacturing method, the inorganic acid or the carboxylic acid is added to the reaction system prior to condensation reacting or when condensation reacting the silicon-containing compound containing a silicon-bonded hydroxyl group and the silicon-containing compound containing a silicon-bonded aminoxy group.

On the other hand, in the present invention, a low-odor organopolysiloxane can also be manufactured by adding the inorganic acid or the carboxylic acid to the reaction system after condensation reacting the silicon-containing compound containing a silicon-bonded hydroxyl group and the silicon-containing compound containing a silicon-bonded aminoxy group. The method for manufacturing a low-odor organopolysiloxane of this aspect comprises the steps of: obtaining a composition comprising an organopolysiloxane obtained by condensation reacting at least one type of a silicon-containing compound containing a silicon-bonded hydroxyl group and at least one type of a silicon-containing compound containing a silicon-bonded aminoxy group; and adding at least one type of an inorganic acid or a carboxylic acid to said composition.

The organopolysiloxane composition of the present invention can optionally comprise a reaction medium such as a solvent, a dispersing medium, or the like. Use of a reaction medium is not necessary but, for example, in cases where the viscosity of the composition is excessively high or, alternately, in cases where it is necessary to increase the dispersibility of the reaction components, a reaction medium such as an inert solvent, a dispersing medium, or the like is preferably used in the reaction. Examples of this inert reaction medium include aqueous media such as water, alcohol, and the like; and non-aqueous media such as hydrocarbon oil, silicone oil, and the like.

In order to avoid the influence of the inorganic acid or the carboxylic acid on the silicon-containing compound containing a silicon-bonded hydroxyl group and/or the silicon-containing compound containing a silicon-bonded aminoxy group, in the method for manufacturing an organopolysiloxane of the present invention, the at least one type of the inorganic acid or the carboxylic acid is preferably added after condensation reacting the at least one type of silicon-containing compound containing a silicon-bonded hydroxyl group and the at least one type of silicon-containing compound containing a silicon-bonded aminoxy group.

The organopolysiloxane obtained through the manufacturing method of the present invention has a high molecular weight and, therefore, in its own right can exhibit superior properties as a raw material for use in cosmetic compositions.

Additionally, with the manufacturing method of the present invention, an amount of volatile low molecular weight cyclic siloxanes such as octamethylcyclotetrasiloxane, decamethylcyclopentasiloxane, dodecamethylcyclohexasiloxane, and the like, which is a by-product of the condensation reaction is small. Therefore, from this perspective as well, the organopolysiloxane composition obtained via the present invention is suitable as a raw material for use in cosmetic compositions.

Regardless of being obtained via the condensation reaction of the silicon-containing compound containing a silicon-bonded hydroxyl group and the silicon-containing compound containing a silicon-bonded aminoxy group, with the organopolysiloxane obtained through the present invention, odor originating from the hydroxylamine that is inevitably produced as a by-product of said condensation reaction is reduced. Therefore, from the perspective of odor as well, the organopolysiloxane composition obtained via the present invention is suitable as a raw material for use in cosmetic compositions.

INDUSTRIAL APPLICABILITY

The organopolysiloxane composition of the present invention has little odor. Additionally, the content of volatile cyclic polysiloxane in the organopolysiloxane composition of the present invention is low and, the molecular weight of the organopolysiloxane included therein is great. As a result, superior properties as cosmetic composition can be exhibited. Therefore, the organopolysiloxane composition of the present invention is particularly useful as a raw material for use in cosmetic compositions.

Moreover, with the method for manufacturing an organopolysiloxane of the present invention, in addition to having reduced odor, the content of volatile cyclic polysiloxane, which can impart discomfort such as a sense of dryness or the like when applied to the skin, is low; and an organopolysiloxane having a high molecular weight can be easily manufactured. Therefore, the organopolysiloxane obtained via the present invention can be used as a raw material for a cosmetic composition for use on a human body, and can exhibit superior properties as a raw material for use in cosmetic compositions.

Volatile cyclic polysiloxanes vaporize in the air and may cause a contact fault in cases where they come in contact with an electric circuit of a semiconductor device or the like. However, the organopolysiloxane composition of the present invention, that is, the organopolysiloxane obtained via the manufacturing method of the present invention has a low content of such volatile low molecular weight polysiloxanes and, therefore, can be suitably used in electric and electronic devices.

EXAMPLES

Hereinafter, the present invention will be described in detail based on Practical Examples and Comparative Examples. However, the present invention is not limited to these Practical Examples. Note that in the descriptions given below "parts" refer to parts by weight and "%" refers to wt %.

Practical Example 1

480 parts of a dimethylpolysiloxane capped at both molecular terminals with hydroxy groups (viscosity: 2,500 mm$^2$/s) represented by the following formula:

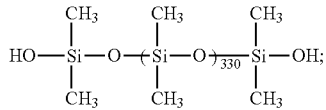

20 parts of a dimethylpolysiloxane capped at both molecular terminals with aminoxy groups represented by the formula $(C_2H_5)_2NO[(CH_3)_2SiO]_6(CH_3)_2SiON(C_2H_5)_2$; 30 parts of a polyoxyethylene-polyoxypropylene block copolymer; and 100 parts of cetyltrimethylammonium chloride (30% aqueous solution) were agitated for 10 minutes and then emulsified. 368.5 parts of water was added thereto and uniformly dispersed. Furthermore, 1 part of phosphoric acid and a preservative were added and uniformly dispersed. The obtained emulsion was held at room temperature for 72 hours and, thereafter, was evaluated for appearance, odor, and the like as described below. Then, the same emulsion was stored at 50° C. for one month and, thereafter, was evaluated for appearance and odor in the same way. The results are shown in Table 1.

Practical Example 2

480 parts of the dimethylpolysiloxane capped at both molecular terminals with hydroxy groups (viscosity: 2,500 mm$^2$/s); 20 parts of a dimethylpolysiloxane capped at both molecular terminals with aminoxy groups represented by the formula $(C_2H_5)_2NO[(CH_3)_2SiO]_6(CH_3)_2SiON(C_2H_5)_2$; 30 parts of a polyoxyethylene-polyoxypropylene block copolymer; and 100 parts of cetyltrimethylammonium chloride (30% aqueous solution) were agitated for 10 minutes and then emulsified. 367.1 parts of water was added thereto and uniformly dispersed. Furthermore, 2.4 parts of acetic acid and a preservative were added and uniformly dispersed. The obtained emulsion was held at room temperature for 72 hours and, thereafter, was evaluated for appearance, odor, and the like as described below. Then, the same emulsion was stored at 50° C. for one month and, thereafter, was evaluated for appearance and odor in the same way. The results are shown in Table 1.

Practical Example 3

380 parts of the dimethylpolysiloxane capped at both molecular terminals with hydroxy groups (viscosity: 2,500 mm$^2$/s); 100 parts of an amino group-containing dimethylpolysiloxane capped at both molecular terminals with hydroxy groups (viscosity: 1,000 mm$^2$/s, amino content: 0.2%) represented by the following formula:

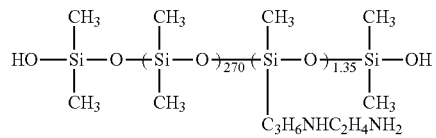

20 parts of a dimethylpolysiloxane capped at both molecular terminals with aminoxy groups represented by the formula $(C_2H_5)_2NO[(CH_3)_2SiO]_6(CH_3)_2SiON(C_2H_5)_2$; 30 parts of a polyoxyethylene-polyoxypropylene block copolymer; and 100 parts of cetyltrimethylammonium chloride (30% aqueous solution) were agitated for 10 minutes and then emulsified. 368.5 parts of water was added thereto and uniformly dispersed. Furthermore, 1 part of phosphoric acid and a preservative were added and uniformly dispersed. The obtained emulsion was held at room temperature for 72 hours and, thereafter, was evaluated for appearance, odor, and the like as described below. Then, the same emulsion was stored at 50° C. for one month and, thereafter, was evaluated for appearance and odor in the same way. The results are shown in Table 1.

Practical Example 4

380 parts of the dimethylpolysiloxane capped at both molecular terminals with hydroxy groups (viscosity: 2,500 mm$^2$/s); 100 parts of the amino group-containing dimethylpolysiloxane capped at both molecular terminals with hydroxy groups (viscosity: 1,000 mm$^2$/s, amino content: 0.2%); 20 parts of a dimethylpolysiloxane capped at both molecular terminals with aminoxy groups represented by the formula $(C_2H_5)_2NO[(CH_3)_2SiO]_6(CH_3)_2SiON(C_2H_5)_2$; 25 parts of a polyoxyethylene-polyoxypropylene block copolymer; 25 parts of methyl lauroyl taurate; and 68.5 parts of water were agitated for 10 minutes and then emulsified. 380 parts of water was added thereto and uniformly dispersed. Furthermore, 1 part of phosphoric acid and a preservative were added and uniformly dispersed. The obtained emulsion was held at room temperature for 72 hours and, thereafter, was evaluated for appearance, odor, and the like as described below. Then, the same emulsion was stored at 50° C. for one month and, thereafter, was evaluated for appearance and odor in the same way. The results are shown in Table 1.

Comparative Example 1

480 parts of the dimethylpolysiloxane capped at both molecular terminals with hydroxy groups (viscosity: 2,500 mm$^2$/s); 20 parts of a dimethylpolysiloxane capped at both molecular terminals with aminoxy groups represented by the formula $(C_2H_5)_2NO[(CH_3)_2SiO]_6(CH_3)_2SiON(C_2H_5)_2$; 30 parts of a polyoxyethylene-polyoxypropylene block copolymer; and 100 parts of cetyltrimethylammonium chloride (30% aqueous solution) were agitated for 10 minutes and then emulsified. 369.5 parts of water and a preservative were added thereto and uniformly dispersed. The obtained emulsion was held at room temperature for 72 hours and, thereafter, was evaluated for appearance, odor, and the like as described below. Then, the same emulsion was stored at 50° C. for one month and, thereafter, was evaluated for appearance and odor in the same way. The results are shown in Table 1.

Comparative Example 2

380 parts of the dimethylpolysiloxane capped at both molecular terminals with hydroxy groups (viscosity: 2,500 mm$^2$/s); 100 parts of the amino group-containing dimethylpolysiloxane capped at both molecular terminals with hydroxy groups (viscosity: 1,000 mm$^2$/s, amino content: 0.2%); 20 parts of a dimethylpolysiloxane capped at both molecular terminals with aminoxy groups represented by the formula $(C_2H_5)_2NO[(CH_3)_2SiO]_6(CH_3)_2SiON(C_2H_5)_2$; 25 parts of a polyoxyethylene-polyoxypropylene block copolymer; 35.7 parts of polyoxyethylene (2 mol) lauryl ether sodium sulfate (70% aqueous solution); and 38.8 parts of water were agitated for 10 minutes and then emulsified. 400 parts of water and a preservative were added thereto and uniformly dispersed. The obtained emulsion was held at room temperature for 72 hours and, thereafter, was evaluated for appearance, odor, and the like as described below. Then, the same emulsion was stored at 50° C. for one month and, thereafter, was evaluated for appearance and odor in the same way. The results are shown in Table 1.

Appearance: The physical state was visually determined.
pH: The pH was measured using a pH meter.
Odor: Determined through olfactory perception.
Particle diameter: Measured using a submicronic light scattering particle diameter measurement device (BECKMAN COULTER K.K.).
Viscosity: A portion of the emulsion was collected and ethyl alcohol was added thereto so as to break down said emulsion. Oil was extracted and the viscosity thereof was measured using a rotating viscometer (R-type viscometer RE100U, manufactured by Toki Sangyo Co., Ltd.; cone rotor: 3°×R7.7; rotation speed: 0.5 rpm).

TABLE 1

| | Practical Example | | | | Comparative Example | |
|---|---|---|---|---|---|---|
| | 1 | 2 | 3 | 4 | 1 | 2 |
| Dimethylpolysiloxane capped at both molecular terminals with hydroxy groups | 48.00 | 48.00 | 38.00 | 38.00 | 48.00 | 38.00 |
| Amino group-containing dimethylpolysiloxane capped at both molecular terminals with hydroxy groups | — | — | 10.00 | 10.00 | — | 10.00 |
| Dimethylpolysiloxane capped at both molecular terminals with aminoxy groups | 2.00 | 2.00 | 2.00 | 2.00 | 2.00 | 2.00 |
| Polyoxyethylene-polyoxypropylene block copolymer | 3.00 | 3.00 | 3.00 | 2.50 | 3.00 | 2.50 |
| Polyoxyethylene (2 mol) lauryl ether sodium sulfate | — | — | — | — | — | 3.57 |
| Methyl lauroyl taurate | — | — | — | 2.50 | — | — |
| Cetyltrimethylammonium chloride (30% aqueous solution) | 10.00 | 10.00 | 10.00 | — | 10.00 | — |
| Phosphoric acid | 0.10 | — | 0.10 | 0.10 | — | — |
| Acetic acid | — | 0.24 | — | — | — | — |
| Preservative | 0.05 | 0.05 | 0.05 | 0.05 | 0.05 | 0.05 |
| Water | 36.85 | 36.71 | 36.85 | 44.85 | 36.95 | 43.88 |
| Evaluation results (after 72 hours storage at room temperature) | | | | | | |
| Appearance | Milky white liquid | | | | | |
| pH | 6.5 | 5.0 | 6.0 | 7.5 | 8.5 | 9.5 |
| Odor | Slight emulsifier odor | | | | Unpleasant amine odor | |
| Particle diameter (nm) | 226 | 226 | 217 | 236 | 226 | 222 |
| Viscosity (mPa·s) | 2990000 | 150000 | Slightly crosslinked polymers | | 3700000 | Slightly crosslinked polymers |
| Evaluation results (after one month storage at 50° C.) | | | | | | |
| Appearance | No change | | | | | |
| Odor | No change | | | | Increase in unpleasant amine odor | |

Reference Example 1

480 parts of the dimethylpolysiloxane capped at both molecular terminals with hydroxy groups (viscosity: 2,500 mm$^2$/s); 20 parts of a dimethylpolysiloxane capped at both molecular terminals with aminoxy groups represented by the formula $(C_2H_5)_2NO[(CH_3)_2SiO]_6(CH_3)_2SiON(C_2H_5)_2$; 25 parts of a polyoxyethylene-polyoxypropylene block copolymer; 35.5 parts of polyoxyethylene (2 mol) lauryl ether sodium sulfate (70% aqueous solution); and 39.5 parts of water were agitated for 10 minutes and then emulsified. 390.0 parts of water was added thereto and uniformly dispersed. The emulsion was stored at room temperature for 72 hours and, thereafter, the polymer in the emulsion was extracted and the viscosity of said polymer was measured to be 210,000 mPa·s. The obtained emulsion is referred to as emulsion A.

Reference Example 2

480 parts of the dimethylpolysiloxane capped at both molecular terminals with hydroxy groups (viscosity: 2,500 mm$^2$/s); 20 parts of a dimethylpolysiloxane capped at both molecular terminals with aminoxy groups represented by the formula $(C_2H_5)_2NO[(CH_3)_2SiO]_6(CH_3)_2SiON(C_2H_5)_2$; 25 parts of a polyoxyethylene-polyoxypropylene block copolymer; and 83 parts of cetyltrimethylammonium chloride (30% aqueous solution) were agitated for 10 minutes and then emulsified. 382 parts of water was added thereto and uniformly dispersed. The emulsion was stored at room temperature for 72 hours and, thereafter, the polymer in the emulsion was extracted and the viscosity of said polymer was measured to be 870,000 mPa·s. The obtained emulsion is referred to as emulsion B.

Practical Examples 5 to 28 and Comparative Examples 3 to 4

The types and amounts of acids and water shown in Tables 2 and 3 were added and mixed with 99 parts of the emulsion A and the emulsion B, respectively, so as to total 100 parts (Practical Examples 5 to 28). Additionally, the amounts of water shown in Tables 2 and 3 were added and mixed with 99 parts of the emulsion A and the emulsion B, respectively, so as to total 100 parts (Comparative Examples 3 to 4). The appearances, pH, and odors of the obtained anionic surfactant-containing emulsions and the obtained cationic surfactant-containing emulsions were evaluated as described above. The results are shown in Table 2.

TABLE 2

|  | Practical Example |  |  |  |  |  |  |  |  |  |  |  | Comparative |
|---|---|---|---|---|---|---|---|---|---|---|---|---|---|
|  | 5 | 6 | 7 | 8 | 9 | 10 | 11 | 12 | 13 | 14 | 15 | 16 | Example 3 |
| Emulsion A | 99.00 | 99.00 | 99.00 | 99.00 | 99.00 | 99.00 | 99.00 | 99.00 | 99.00 | 99.00 | 99.00 | 99.00 | 99.00 |
| Hydrochloric acid | 0.16 | 0.32 | 0.47 | — | — | — | — | — | — | — | — | — | — |
| Acetic acid | — | — | — | 0.10 | 0.20 | 0.30 | — | — | — | — | — | — | — |
| Lactic acid | — | — | — | — | — | — | 0.15 | 0.30 | 0.45 | — | — | — | — |
| Phosphoric acid | — | — | — | — | — | — | — | — | — | 0.10 | 0.20 | 0.30 | — |
| Water | 0.84 | 0.68 | 0.53 | 0.90 | 0.80 | 0.70 | 0.85 | 0.70 | 0.55 | 0.90 | 0.80 | 0.70 | 1.00 |
| Evaluation results |  |  |  |  |  |  |  |  |  |  |  |  |  |
| Appearance | Milky white liquid |  |  |  |  |  |  |  |  |  |  |  |  |
| pH | 6.10 | 5.65 | 4.94 | 7.35 | 5.67 | 5.25 | 6.33 | 5.77 | 4.60 | 6.39 | 6.04 | 5.58 | 8.93 |
| Odor | Slight odor |  |  |  |  |  |  |  |  |  |  |  | Strong unpleasant odor |
|  | Emulsifier odor |  |  |  |  |  |  |  |  |  |  |  | Amine odor Emulsifier odor |

TABLE 3

|  | Practical Example |  |  |  |  |  |  |  |
|---|---|---|---|---|---|---|---|---|
|  | 17 | 18 | 19 | 20 | 21 | 22 | 23 | 24 |
| Emulsion B | 99.00 | 99.00 | 99.00 | 99.00 | 99.00 | 99.00 | 99.00 | 99.00 |
| Hydrochloric acid | 0.16 | 0.32 | 0.47 | — | — | — | — | — |
| Acetic acid | — | — | — | 0.10 | 0.20 | 0.30 | — | — |
| Lactic acid | — | — | — | — | — | — | 0.15 | 0.30 |
| Phosphoric acid | — | — | — | — | — | — | — | — |
| Water | 0.84 | 0.68 | 0.53 | 0.90 | 0.80 | 0.70 | 0.85 | 0.70 |

TABLE 3-continued

| | Evaluation results | | | | | | | |
|---|---|---|---|---|---|---|---|---|
| Appearance | Milky white liquid | | | | | | | |
| pH | 6.04 | 5.55 | 4.72 | 6.05 | 5.89 | 5.38 | 6.20 | 5.67 |
| Odor | | | | | Slight odor | | | |
| | | | | | Emulsifier odor | | | |

| | | Practical Example | | | | Comparative |
|---|---|---|---|---|---|---|
| | | 25 | 26 | 27 | 28 | Example 4 |
| | Emulsion B | 99.00 | 99.00 | 99.00 | 99.00 | 99.00 |
| | Hydrochloric acid | — | — | — | — | — |
| | Acetic acid | — | — | — | — | — |
| | Lactic acid | 0.45 | — | — | — | — |
| | Phosphoric acid | — | 0.10 | 0.20 | 0.30 | — |
| | Water | 0.55 | 0.90 | 0.80 | 0.70 | 1.00 |
| | Evaluation results | | | | | |
| Appearance | | Milky white liquid | | | | |
| pH | | 5.35 | 6.09 | 6.02 | 5.51 | 8.46 |
| Odor | | | Slight odor | | | Strong unpleasant odor |
| | | | Emulsifier odor | | | Amine odor Emulsifier odor |

Reference Example 3

A liquid compound C for use in shampoos was prepared by mixing the components shown in Table 4.

TABLE 4

| Raw material | Compounded amount (parts) |
|---|---|
| Water | 30 |
| Cationized cellulose | 10 |
| Disodium ethylenediaminetetraacetate salt | 0.1 |
| Glycerin | 2 |
| Coconut oil fatty acid monoethanol amide | 2 |
| Glycol distearate | 2 |
| Polyoxyethylene (2) lauryl ether sodium sulfate | 30 |
| Polyoxyethylene (6) lauryl ether sodium carboxylate | 10 |
| Coconut oil fatty acid amido propyl betaine | 10 |

TABLE 4-continued

| Raw material | Compounded amount (parts) |
|---|---|
| Cationized polymer | 3 |
| Methylisothiazoline | 0.1 |

Practical Examples 29 to 33 Comparative Examples 5 to 6, and Control 1

The types and amounts of emulsions shown in Table 5 were added and mixed with 99 parts of the liquid compound C for use in shampoos so as to total 100 parts (Practical Examples 29 to 33 and Comparative Examples 5 to 6). Additionally, the amounts of water shown in Table 5 were added and mixed to 99 parts of the liquid compound C for use in shampoos so as to total 100 parts (Control 1). Odor was evaluated as described above immediately after preparing the shampoo, and also after storing the shampoo for seven days at 50° C. The results are shown in Table 5.

TABLE 5

| | Practical Example | | | | | Comparative Example | | |
|---|---|---|---|---|---|---|---|---|
| | 29 | 30 | 31 | 32 | 33 | 5 | 6 | Control 1 |
| Shampoo use liquid compound C | 99.0 | 99.0 | 99.0 | 99.0 | 99.0 | 99.0 | 99.0 | 99.0 |
| Emulsion of Practical Example 5 | 1.0 | — | — | — | — | — | — | — |
| Emulsion of Practical Example 8 | — | 1.0 | — | — | — | — | — | — |
| Emulsion of Practical Example 13 | — | — | 1.0 | — | — | — | — | — |
| Emulsion of Practical Example 16 | — | — | — | 1.0 | — | — | — | — |
| Emulsion of Practical Example 4 | — | — | — | — | 1.0 | — | — | — |
| Emulsion of Comparative | — | — | — | — | — | 1.0 | — | — |

TABLE 5-continued

|  | Practical Example | | | | | Comparative Example | | Control 1 |
|---|---|---|---|---|---|---|---|---|
|  | 29 | 30 | 31 | 32 | 33 | 5 | 6 |  |
| Example 2 Emulsion of Comparative Example 3 | — | — | — | — | — | — | 1.0 | — |
| Water | — | — | — | — | — | — | — | 1.0 |
| Evaluation results | | | | | | | | |
| Odor: Immediately after preparation | Slight emulsifier odor | | | | | | | |
| Odor: After 7 days of storage at 50° C. | No change Good | | | | | Amine odor Unpleasant | | No change |

Reference Example 4

A liquid compound D for use in conditioners was prepared by mixing the components shown in Table 6.

TABLE 6

| Raw material | Compounded amount (parts) |
|---|---|
| Stearyl trimethylammonium chloride | 1.8 |
| Cetyl alcohol | 2.4 |
| Octyldodecanol | 0.5 |
| Cetyl ethylhexanoate | 0.6 |
| Squalane | 0.2 |
| Glycerin | 2.0 |
| Methylisothiazoline | 0.1 |
| Water | 77.4 |

Practical Examples 34 to 38 Comparative Example 7, and Control 2

The types and amounts of emulsions shown in Table 7 were added and mixed with 85.0 parts of the liquid compound D for use in conditioners so as to total 100 parts (Practical Examples 34 to 38 and Comparative Example 7). Additionally, the amounts of water shown in Table 7 were added and mixed to 99 parts of the liquid compound D for use in conditioners so as to total 100 parts (Control 2). Odor was evaluated as described above immediately after preparing the conditioner, and also after storing the conditioner for seven days at 50° C. The results are shown in Table 7.

TABLE 7

|  | Practical Example | | | | | Comparative | |
|---|---|---|---|---|---|---|---|
|  | 34 | 35 | 36 | 37 | 38 | Example 7 | Control 2 |
| Conditioner use liquid compound D | 85.0 | 85.0 | 85.0 | 85.0 | 85.0 | 85.0 | 85.0 |
| Emulsion of Practical Example 17 | 2.4 | — | — | — | — | — | — |
| Emulsion of Practical Example 20 | — | 2.4 | — | — | — | — | — |
| Emulsion of Practical Example 25 | — | — | 2.4 | — | — | — | — |
| Emulsion of Practical Example 28 | — | — | — | 2.4 | — | — | — |
| Emulsion of Practical Example 3 | — | — | — | — | 2.4 | — | — |
| Emulsion of Comparative Example 4 | — | — | — | — | — | 2.4 | — |
| Water | 12.6 | 12.6 | 12.6 | 12.6 | 12.6 | 12.6 | 15.0 |
| Evaluation results | | | | | | | |
| Odor: Immediately after preparation | Slight emulsifier odor | | | | | | |
| Odor: After 7 days of storage at 50° C. | No change Good | | | | | Amine odor Unpleasant | No change |

Reference Example 5

375 parts of the dimethylpolysiloxane capped at both molecular terminals with hydroxy groups (viscosity: 2,500 mm²/s); 25 parts of a dimethylpolysiloxane capped at both molecular terminals with aminoxy groups represented by the formula $(C_2H_5)_2NO[(CH_3)_2SiO]_6(CH_3)_2SiON(C_2H_5)_2$; 20 parts of a polyoxyethylene-polyoxypropylene block copolymer; 54 parts of α-olefin (C=12) sodium sulfonate (35% aqueous solution); and 16 parts of water were agitated for 10 minutes and then emulsified. 500 parts of water was added thereto and uniformly dispersed. The emulsion was stored at room temperature for 72 hours and, thereafter, the polymer in the emulsion was extracted and the viscosity of said polymer was measured to be 420,000 mPa·s. The obtained emulsion is referred to as emulsion C.

Practical Examples 39 to 42 and Comparative Example 8

The types and amounts of acids and water shown in Table 8 were added and mixed with 99.0 parts of the emulsion C so as to total 100 parts (Practical Examples 39 to 42). Additionally, the amounts of water shown in Table 8 were added and mixed with 99.0 parts of the emulsion C so as to total 100 parts (Comparative Example 8). The appearances and odors of the obtained emulsions immediately after preparation were evaluated as described above. Additionally, odor was evaluated as described above after storing the obtained emulsions for five days at 40° C.

The results are shown in Table 8.

TABLE 8

|  | Practical Example 39 | Practical Example 40 | Practical Example 41 | Practical Example 42 | Comparative Example 8 |
|---|---|---|---|---|---|
| Emulsion C | 99.00 | 99.00 | 99.00 | 99.00 | 99.00 |
| Citric acid | 0.30 | 0.60 | — | — | — |
| L-glutamate | — | — | 0.50 | 1.00 | — |
| Water | 0.70 | 0.40 | 0.50 | — | 1.00 |
| Evaluation results | | | | | |
| Appearance | Milky white liquid | Milky white liquid | Milky white liquid | Milky white liquid | Milky white liquid |
| Odor: Immediately after preparation | Slight odor | Slight odor | Slight odor | Slight odor | Strong unpleasant odor |
|  | Emulsifier odor | Emulsifier odor | Emulsifier odor | Emulsifier odor | Amine odor and emulsifier odor |
| Odor: After 5 days of storage at 40° C. | Slight odor | Slight odor | Slight odor | Slight odor | Stronger unpleasant dodor |
|  | Emulsifier odor | Emulsifier odor | Emulsifier odor | Emulsifier odor | Amine odor and emulsifier odor |

wherein $R^4$ is an oxygen atom, a sulfur atom, or a divalent organic group.

The invention claimed is:

1. An organopolysiloxane composition comprising:

at least one inorganic acid or carboxylic acid, and an organopolysiloxane obtained by condensation reaction of at least one silicon-containing compound containing a silicon-bonded hydroxyl group and at least one silicon-containing compound containing a silicon-bonded aminoxy group, wherein said organopolysiloxane composition comprises not less than 0.3 mol of the inorganic acid or the carboxylic acid per 1 mol of the silicon-containing compound containing the silicon-bonded aminoxy group, wherein the silicon-containing compound containing a silicon-bonded aminoxy group is a diorganopolysiloxane capped at both molecular terminals with diorganoaminoxysilyl groups, a diorganosiloxane-polyoxyalkylene block copolymer capped at both molecular terminals with diorganoaminoxysilyl groups, an aminoxyorganopolysiloxane capped at both molecular terminals with triorganosilyl groups, or a diorganosiloxane-aminoxyorganosiloxane copolymer capped at both molecular terminals with triorganosilyl groups, and wherein the silicon-bonded aminoxy group is —ON($R^3$)$_2$, wherein $R^3$ are each independently a hydrogen atom or a substituted or unsubstituted, straight, branched, or cyclic monovalent hydrocarbon group having from 1 to 30 carbons, or a group represented by the following formula:

2. The composition according to claim 1, wherein the composition includes the inorganic acid and the inorganic acid is selected from the group consisting of hydrochloric acid, sulfuric acid, nitric acid, phosphoric acid, and carbonic acid.

3. The composition according to claim 1, wherein the silicon-containing compound containing a silicon-bonded hydroxyl group is a diorganopolysiloxane capped at both molecular terminals with diorganohydroxysilyl groups.

4. The composition according to claim 1, wherein $R^4$ is the divalent organic group and the divalent organic group is —N($R^5$)—, wherein $R^5$ is a hydrogen atom or a substituted or unsubstituted, straight, branched, or cyclic monovalent hydrocarbon group having from 1 to 30 carbons; a substituted or unsubstituted, straight or branched divalent hydrocarbon group having from 1 to 20 carbons; or a substituted or unsubstituted, straight or branched divalent hydrocarbon group comprising at least one hetero-atom and having from 1 to 20 carbons.

5. The composition according to claim 1, further comprising at least one surfactant.

6. The composition according to claim 1, further comprising water.

7. The composition according to claim 6, wherein the composition is an emulsion.

8. A cosmetic composition comprising the composition according to claim 1.

9. The cosmetic composition according to claim 8, wherein the cosmetic composition is a hair care cosmetic composition.

10. A method for manufacturing a low-odor organopolysiloxane, the method comprising:

reacting at least one silicon-containing compound containing a silicon-bonded hydroxyl group and at least one silicon-containing compound containing a silicon-bonded aminoxy group via a condensation reaction in the presence of at least one inorganic acid or carboxylic acid, wherein said organopolysiloxane composition comprises not less than 0.3 mol of the inorganic acid or the carboxylic acid per 1 mol of the silicon-containing compound containing the silicon-bonded aminoxy group, wherein the silicon-containing compound containing a silicon-bonded aminoxy group is a diorganopolysiloxane capped at both molecular terminals with diorganoaminoxysilyl groups, a diorganosiloxane-polyoxyalkylene block copolymer capped at both molecular terminals with diorganoaminoxysilyl groups, an aminoxyorganopolysiloxane capped at both molecular terminals with triorganosilyl groups, or a diorganosiloxane- aminoxyorganosiloxane copolymer capped at both molecular terminals with triorganosilyl, and wherein the silicon-bonded aminoxy group is $-ON(R^3)_2$, wherein $R^3$ are each independently a hydrogen atom or a substituted or unsubstituted, straight, branched, or cyclic monovalent hydrocarbon group having from 1 to 30 carbons, or a group represented by the following formula:

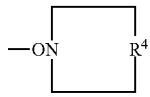

wherein $R^4$ is an oxygen atom, a sulfur atom, or a divalent organic group.

11. A method for manufacturing a low-odor organopolysiloxane, the method comprising:

obtaining a composition comprising an organopolysiloxane obtained by reacting at least one silicon-containing compound containing a silicon-bonded hydroxyl group and at least one silicon-containing compound containing a silicon-bonded aminoxy group via a condensation reaction, wherein the silicon-containing compound containing a silicon-bonded aminoxy group is a diorganopolysiloxane capped at both molecular terminals with diorganoaminoxysilyl groups, a diorganosiloxane-polyoxyalkylene block copolymer capped at both molecular terminals with diorganoaminoxysilyl groups, an aminoxyorganopolysiloxane capped at both molecular terminals with triorganosilyl groups, or a diorganosiloxane-aminoxyorganosiloxane copolymer capped at both molecular terminals with triorganosilyl groups; and adding at least one inorganic acid or carboxylic acid to said composition, wherein said organopolysiloxane composition comprises not less than 0.3 mol of the inorganic acid or the carboxylic acid per 1 mol of the silicon-containing compound containing the silicon-bonded aminoxy group, and wherein the silicon-bonded aminoxy group is $-ON(R^3)_2$, wherein $R^3$ are each independently a hydrogen atom or a substituted or unsubstituted, straight, branched, or cyclic monovalent hydrocarbon group having from 1 to 30 carbons, or a group represented by the following formula:

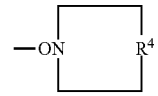

wherein $R^4$ is an oxygen atom, a sulfur atom, or a divalent organic group.

* * * * *